United States Patent
Pipino (10) Patent No.: US 10,598,613 B2
(45) Date of Patent: Mar. 24, 2020

(54) NON-DESTRUCTIVE X-RAY INSPECTION MACHINE, DEVICES PROVIDED FOR SUCH MACHINE AND METHOD FOR OPERATING THE SAME

(71) Applicant: Dylog Italia S.P.A., Turin (IT)

(72) Inventor: Marco Pipino, Turin (IT)

(73) Assignee: DYLOG ITLALIA S.P.A., Turin (IT)

( * ) Notice: Subject to any disclaimer, the term of this patent is extended or adjusted under 35 U.S.C. 154(b) by 111 days.

(21) Appl. No.: 15/579,813

(22) PCT Filed: May 27, 2016

(86) PCT No.: PCT/IB2016/053125
§ 371 (c)(1),
(2) Date: Dec. 5, 2017

(87) PCT Pub. No.: WO2016/203330
PCT Pub. Date: Dec. 22, 2016

(65) Prior Publication Data
US 2018/0356352 A1 Dec. 13, 2018

(30) Foreign Application Priority Data
Jun. 16, 2015 (IT) .................. 102015000024393

(51) Int. Cl.
*G01N 23/04* (2018.01)
*G01N 23/083* (2018.01)
(Continued)

(52) U.S. Cl.
CPC ......... *G01N 23/083* (2013.01); *B07C 5/3416* (2013.01); *G01N 23/04* (2013.01);
(Continued)

(58) Field of Classification Search
CPC ...... G01N 23/083; G01N 23/04; G01N 23/10; G01N 2223/643; G01V 5/0016; B07C 5/3416
See application file for complete search history.

(56) References Cited

U.S. PATENT DOCUMENTS 4,025,202 A * 5/1977 Deane ................ G01N 21/9045
356/239.4
6,005,912 A 12/1999 Ocleppo
(Continued)

FOREIGN PATENT DOCUMENTS

JP 2006-214725 A 8/2006

*Primary Examiner* — Kiho Kim
(74) *Attorney, Agent, or Firm* — Howson & Howson LLP (57) ABSTRACT

Non-destructive X-ray inspection machine for individually packaged products having a bottom and a lid or cap in separate zones. The machine comprises a conveying apparatus having a transport plane adapted to convey products with the bottom resting on the transport plane, at least two X-ray emitters adapted to emit X-rays so that X-rays pass through the products at a top-to-down angle and at a down-to-top angle, respectively, in an inspection zone comprised in the transport plane. In the machine, at least one of the two emitters is freely adjustable in height and/or orientable in angle, within a predetermined range, relative to the transport plane, whereby the bottom of the product is inspectable without the X-rays of the two emitters intercepting the lid or cap of the products and optimal projection of the bottom of the product can be obtained.

16 Claims, 6 Drawing Sheets

(51) Int. Cl.
*G01V 5/00* (2006.01)
*B07C 5/34* (2006.01)
*G01N 23/10* (2018.01)

(52) U.S. Cl.
CPC ........... *G01N 23/10* (2013.01); *G01V 5/0016* (2013.01); *G01N 2223/643* (2013.01)

(56) References Cited

U.S. PATENT DOCUMENTS

| | | | |
|---|---|---|---|
| 6,049,585 | A | 4/2000 | Ocleppo |
| 6,155,408 | A | 12/2000 | Heuft et al. |
| 6,922,459 | B2 | 7/2005 | Pipino |
| 7,106,827 | B2 * | 9/2006 | Heuft .................... B07C 5/3408 378/57 |
| 9,727,961 | B2 * | 8/2017 | Wang ....................... G01T 7/005 |
| 2002/0071520 | A1 | 6/2002 | Springer et al. |
| 2005/0105680 | A1 | 5/2005 | Nabors et al. |
| 2006/0056583 | A1 | 3/2006 | Heuft et al. |
| 2008/0063148 | A1 | 3/2008 | Kabumoto |
| 2010/0020927 | A1 | 1/2010 | Gilevich et al. |
| 2011/0019796 | A1 | 1/2011 | Wuestenbecker et al. |
| 2012/0128133 | A1 | 5/2012 | King |
| 2015/0144538 | A1 * | 5/2015 | Lehmann ............... G01N 23/18 209/589 |

\* cited by examiner

Fig. 7

NON-DESTRUCTIVE X-RAY INSPECTION MACHINE, DEVICES PROVIDED FOR SUCH MACHINE AND METHOD FOR OPERATING THE SAME

TECHNICAL FIELD

The present invention relates generally to a non-destructive X-ray inspection machine for inspecting individually packaged products.

More particularly, the present invention relates to an X-ray inspection machine for individually packaged food products or pharmaceuticals, such as for instance: metal cans, glass jars, glass vials, rigid containers made of plastics or paper, and so on.

The present invention further relates to devices provided in the inspection machine for making operation thereof effective.

BACKGROUND ART

Non-destructive X-ray inspection machines for inspecting packaged products or, more simply, products, which hereinafter are intended, unless otherwise stated, as referring to the combination of the container and its content, are known.

For instance, the document US2006/0056583 A1 discloses a device for X-ray inspection of containers filled with products, for example beverages, in order to detect foreign bodies in such products, particularly at the bottom of the products.

According to this known document, the products to be inspected travel in line in a transport direction, handled by a handling system along a transport plane, and each product is inspected individually for detecting foreign bodies, which are characterized by having a different density with respect to the product density.

In particular, the known device has two X-ray beam emitters or sources arranged at predetermined positions above and below the transport plane, respectively, and arranged at an angle of 90 degrees of the beams emitted by both emitters when measured relative to the transport direction of the products.

The known device further comprises one or more sensors that are arranged beyond the goods to be inspected and are configured for receiving the X-rays after passing through the products.

The known device provides that the handling system consists of an X-ray transparent conveyor belt and two mutually facing, parallel straps configured for keeping the product by exerting a pressure against the lateral walls of the container, handling the products inside the device in which the inspection is carried out and transferring the products from the device to a conveying system outside the device.

The prior art presents some technical problems.

A first problem lies in the fact that the arrangement of the X-ray emitters above and below the transport plane does not guarantee the detection of foreign bodies, for example, at the upper part of the transported product.

The configuration proposed by the prior art document, which provides for angles between the emitters and the transport plane such that the center of the beams are tangent to the curvature of the bottom of the container, further has some drawbacks, as it is applicable solely to containers that are very high relative to their diameters. It is to be noted that, on the contrary, said configuration is not effective when the diameter of the products is large relative to their height, as at the proposed angle the metal cap of the container often overlaps the bottom in the obtained image, thus making it difficult to detect foreign bodies.

Another problem relates to the angle of 90 degrees of the beams emitted by both emitters relative to the transport direction of the products. Such angle, though simplifying the mechanical manufacturing of the system and the handling of the products, involves that the projection of a foreign body situated near the projection of a vertical wall of the container in one of the captured images is in the same position also in the other one and is consequently difficult to be detected because of the difficulty of separating, by means of numerical methods of image analysis, the projection of the foreign body from the projection of the vertical wall of the container, which is made for instance of glass or metal and is therefore radio-opaque.

A further problem relates generally to the use of straps for effecting transfer of the product onto and from the X-ray transparent inspection belt. Indeed, the supporting structure consisting of mutually facing straps is mechanically complex, differently transparent to X-rays and requires to be adjusted both in height and width in case it has to operate effectively on products with different diameter/height.

For instance, higher products need to be dragged by straps arranged at a higher position, whereas products with different diameters make it necessary that the surfaces of the straps are moved away from/brought close to one another.

A still further problem arises out of the fact that the straps, keeping the products by exerting a pressure against the lateral walls of the container, may damage or otherwise alter a label, if present, especially when this has been placed on the container in the step immediately prior to detection.

Solutions meant to handle/rotate the goods along the inspection belt for recording different images of each product taken from different perspectives are also known form other patent documents, for example from the patent U.S. Pat. No. 6,155,408.

According to such known solutions, it is provided that the walls of the container are acted upon for rotating or tilting it; as a consequence, also these known solutions suffer from the problems discussed above relating to the use of straps.

The Applicant has further observed that the rotation of the container does not guarantee simultaneous rotation of the product contained therein (and of the possibly present foreign body to be detected), especially when the content is a liquid.

From patent document EP 2256069 A1 a conveying apparatus is also known, which is to be used in non-destructive X-ray inspection machines for inspecting products and consists of a slat conveyor belt configured for providing a uniform print in the X-ray image.

This kind of conveying apparatus, even if it does not seem to solve one of the problems set forth above, has the problem of constituting a quite complex structure, more expensive in its manufacturing, generally having a more delicate structure and, in particular, being less versatile, as it is made especially for the indicated use.

In general, the Applicant has observed that the cited prior art is unable to effectively solve the problems set forth above.

SUMMARY OF THE INVENTION

The object of the present invention is to solve the aforesaid problems of prior art.

This object is achieved with the non-destructive X-ray machine for inspecting individually packaged products as claimed.

The present invention further relates to the devices provided in the machine as well as to the method of operation of the machine.

The claims form an integral part of the technical teaching provided herein in relation to the invention.

The following brief description of the invention is given for proving a basic understanding of some aspects of the invention.

This brief description is not an extensive description and as such it is not to be understood as being adapted to identify key or critical elements or to outline the scope of the invention. Its only purpose is to present some concepts of the invention in simplified form as an anticipation of the detailed description provided below.

According to a feature of a preferred embodiment of the invention, the invention relates to an inspection machine in which there are provided at least to X-ray emitters configured for passing top-to-down and down-to-top, respectively, through the products arranged on a transport plane and in which at least one of the X-ray emitters is freely adjustable, within a predetermined range, relative to the transport plane.

According to a further feature of the present invention, the machine further comprises a third X-ray emitter freely adjustable within a predetermined range and configured for passing through the products in a direction orthogonal to the transport plane.

According to another feature of the present invention, the machine comprises a conveying apparatus having at least three conveyor belts arranged end-to-end in cascade.

BRIEF DESCRIPTION OF THE DRAWINGS

These and other features and advantages of the present invention will become apparent from the following description of preferred embodiments given by way of non-limiting example with reference to the accompanying drawings, in which elements denoted by same or similar reference numbers designate elements having same or similar function and construction, and in which.

DESCRIPTION OF PREFERRED EMBODIMENTS

Figure 1:
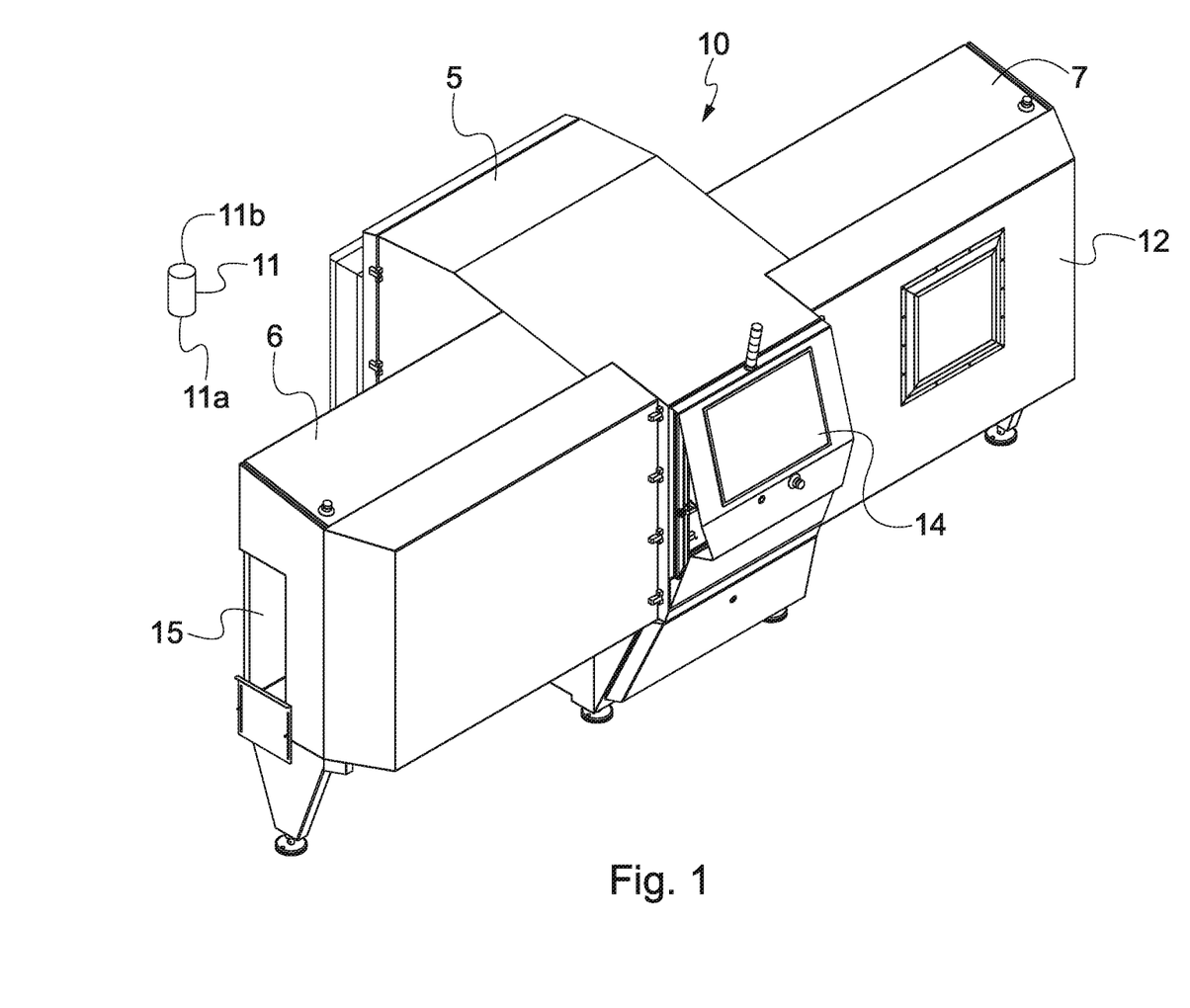
FIG. 1 shows an overall view of an inspection machine for non-destructive X-ray inspection.

Referring to FIG. 1, an X-ray inspection machine (machine) 10 is configured for inspecting packaged products (products) 11 filled up to a certain level, and providing an X-ray image of such products.

The machine, in the preferred embodiment, has an architecture comprising, preferably, a central body 5 and two covers 6 and 7, respectively, all essentially made of a material impermeable to X-rays, of known type, a tunnel 15, configured for enabling transport of the products 11 on a transport plane 44 and along a transport direction, at a predetermined speed, and a monitor (HMI—Human Machine Interface) 14, per se known, preferably located at an inspection zone 16 inside the machine and, preferably, at the main body 5.

According to the preferred embodiment, the machine 10 comprises at its inside three independent X-ray emitters (emitters or sources) 21, 22, 23, for example of the fan beam type, aligned with three X-ray sensors (sensors) 31, 32, 33, for example of the linear type, capable of obtaining, in use, a set of three radiographic images (radiographies) of each product traveling through the tunnel 15 of the machine 10 and passed through by the X-ray beam or useful beam emitted by the emitters.

Figure 4:
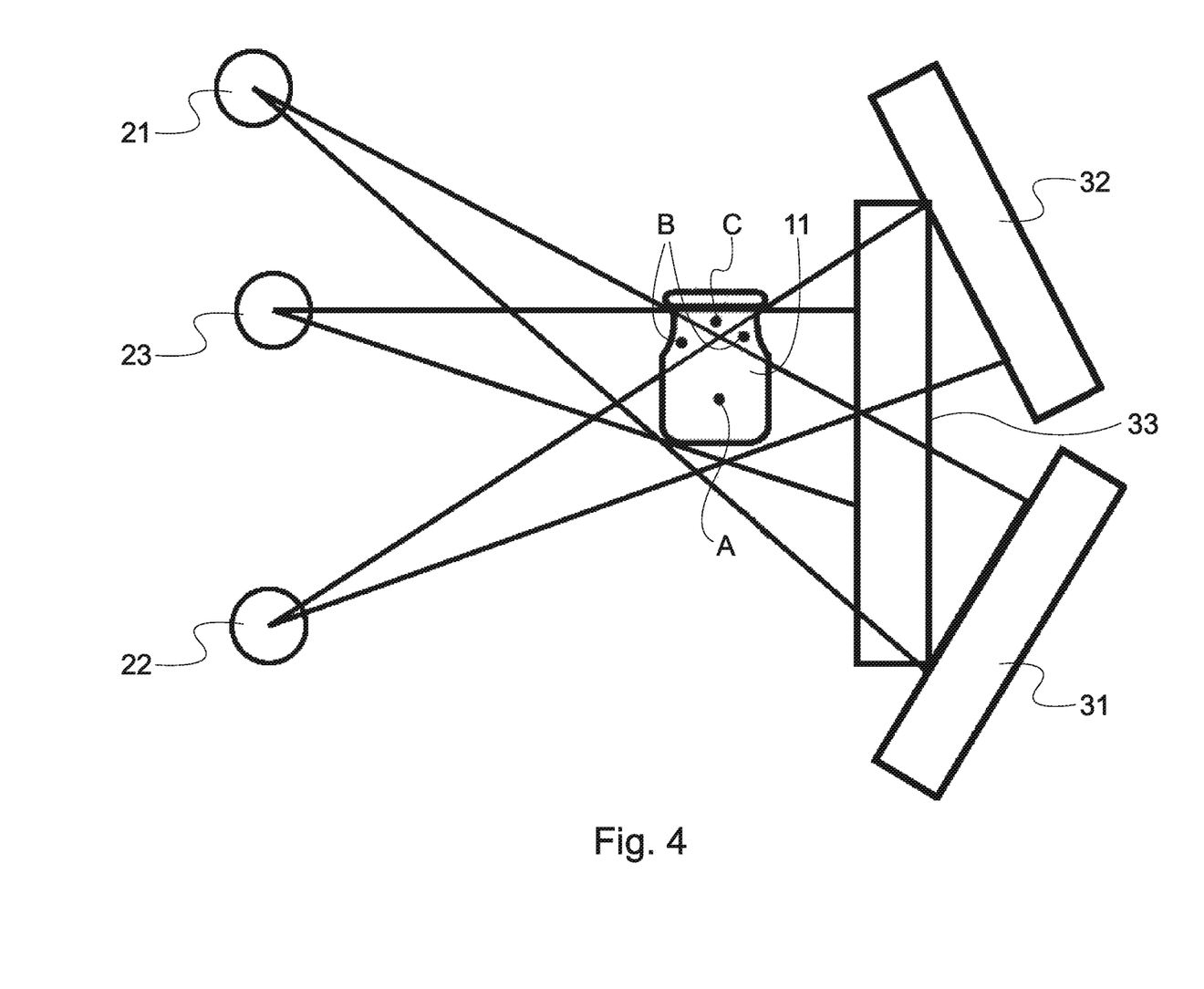
FIG. 4 schematically shows inspection zones A, B, C of a product that can be reached by the machine of the present invention configured with three X-ray emitters or sources.

According to the exemplary embodiment of FIG. 4, there is provided, for example, a zone A in which three images or views are provided, a zone B in which two images or views are provided and a zone C in which a single image or view is provided.

Preferably, the X-ray emitters 21, 22, 23, of known type, for example of the metal-ceramic type Model MXR 100/20 from the Company COMET, consist of three devices, each having for instance a ray-generating tube with small focus arranged for emitting an X-ray useful beam, a high voltage cable and a high voltage generator.

The tubes, for example of the metal-ceramic type constitute the emitters 21, 22, 23 and are connected, through high voltage cables, to the high voltage generators arranged, preferably, at the base of the machine body 12, in a fixed position.

The emitters preferably have ray-generating tubes that have a small focus spot, for example smaller than 1 mm, and allow relative freedom of movement in height and/or angle, as will be described in detail below, on a plane substantially orthogonal to the transport plane, relative to the X-ray sensors 31, 32, 33, without jeopardizing the characteristics of inspection quality; for instance, the emitters are, preferably, of the metal-ceramic type.

According to further embodiments, the X-ray emitters can be made of ceramics or glass, without departing from the scope of the description and claims.

The preferential use of X-ray emitters with small focus spot allows high freedom in arranging the corresponding ray-generating tube, the product to be inspected and the sensor. In fact, the Applicant has found that, assuming as 100% the distance of the sensor from the tube, it is possible, for example, to place the product 11 at distances from the tube ranging between values of 33% and values close to 100% (product adjoining the sensor), without such positioning involving a significant blurring of edges of the obtained image of the product.

Preferably, the machine is applicable to the inspection of cylindrical or sub-cylindrical products, conveyed in the tunnel 15 to the inspection zone 16, by means of a conveying apparatus 40 comprising, preferably, three conveyor belts 41, 42, 43 (FIG. 5 and FIG. 6), as will be described in detail below.

Preferably, the products are arranged, in use, placed on the conveyor belts in such a way that their main axis is in vertical position relative to a horizontal supporting plane coinciding with the transport plane 44 defined by the conveyor belts 41, 42, 43.

Figure 2:
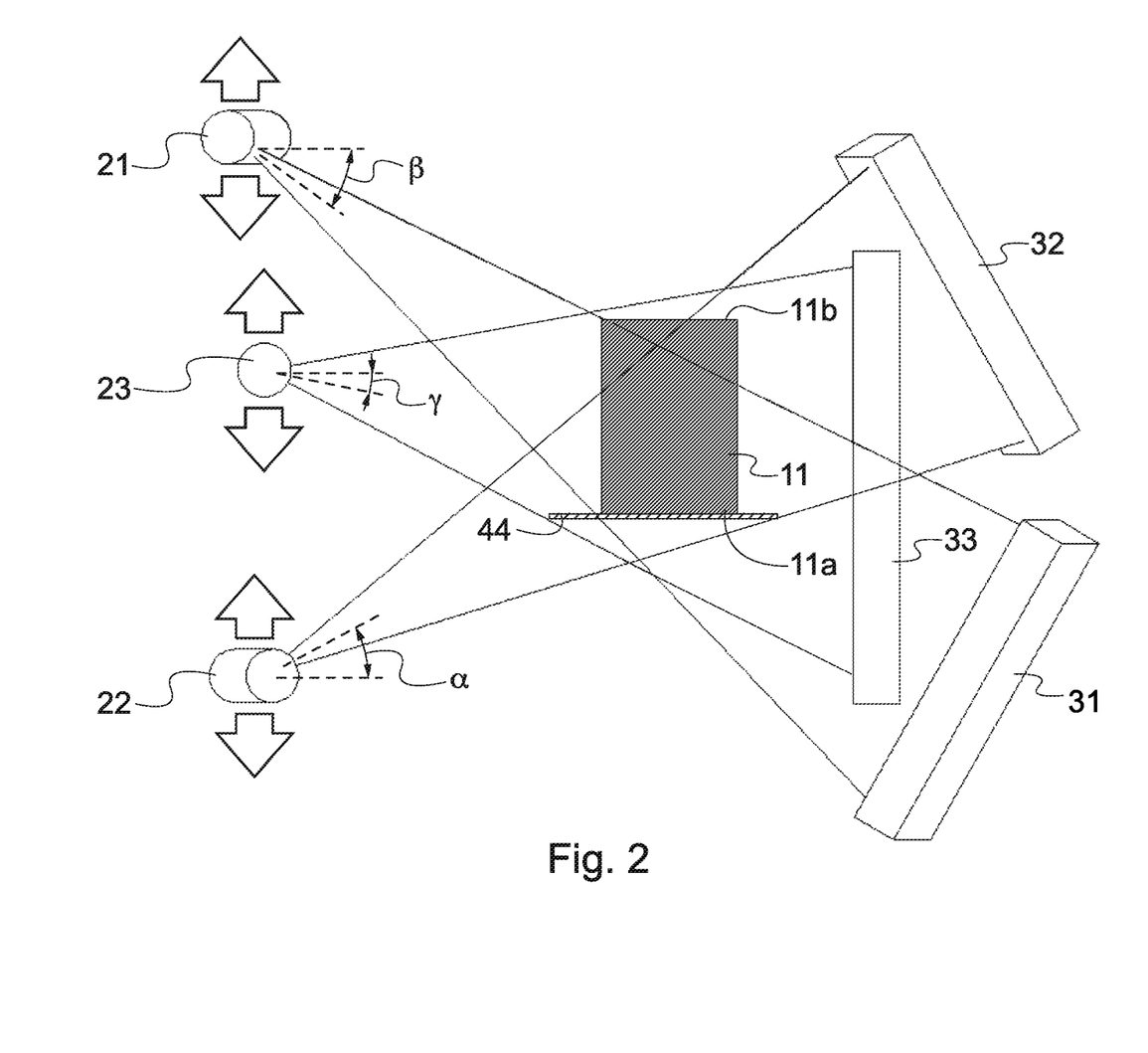
FIG. 2 is a schematic illustration of pairs of X-ray emitters/sensors in a view orthogonal to the movement or transport direction of the products as provided in the machine of FIG. 1.

According to the preferred embodiment, it is provided that a first emitter 21 and a second emitter 22 (FIG. 2, FIG. 3) are arranged above and below the horizontal supporting plane of the products, respectively, so that, in use, the beam of one emitter passes top-to-down and the beam of the other emitter passes down-to-top through the products 11.

This configuration allows to inspect the base or bottom 11a of the product from opposite direction, thus guaranteeing utmost quality and safety in detecting bodies foreign to the product that have settled on the bottom of the product.

According to the preferred embodiment, it is further provided that a third emitter 23 is arranged on a vertical plane, orthogonal to the horizontal supporting plane of the products to be inspected and to the conveying apparatus, and is for instance aligned to the upper zone of the product, preferably at the filling level.

According to further embodiments, this third emitter may be omitted.

When the third emitter is provided, preferably this can be motor-driven, so as to allow exact alignment thereof with the filling level of the product or upper zone of the product.

The configuration with three emitters allows to inspect also the upper zone of the product, for example the zone in which a cap 11b is provided, so as to ensure utmost quality and safety in detecting parts foreign to the product also in the upper zone of the product.

The alignment with the filling level, which alignment is preferable, allows to obtain optimal separation between the image of the content and that of the container cap, thus making analysis easier in this area.

In the preferred embodiment, it is provided that the height and/or direction of each X-ray emitter 21, 22 e 23, on a plane substantially orthogonal to the transport plane 44, can be varied depending, for instance, on the dimensional characteristics of the product to be inspected, especially of its bottom 11a and its height.

For example, handling can be accomplished by making the emitter holder slide on flat or cylindrical guides, preferably graduated, which allow the translatory motion and the fixing of one or more emitters in the selected position.

Similarly, the emitter holder can allow to rotate the emitter according to the selected angle and to retain it in position, for example mechanically by means of tightening screws, or automatically by locking a motor-driven handling system.

For example, the first X-ray emitter 21, in an upper position (FIG. 2) with respect to the horizontal supporting plane, can be adjusted at a height and/or oriented at an angle β, measured from the bisector of the emitted useful beam relative to the horizontal plane, comprised between −18 and −55 degrees.

The second emitter 22, in a lower position with respect to the horizontal supporting plane, can be adjusted at a height and/or oriented at an angle α, measured from the bisector of the emitted useful beam relative to the horizontal plane, comprised between +18 e +55 degrees.

The third emitter 23, arranged on a substantially vertical plane, orthogonal to the horizontal supporting plane, can be adjusted at a height and/or oriented at an angle γ, measured from the bisector of the emitted useful beam relative to the horizontal plane, comprised between 0 e −20 degrees.

In the preferred embodiment, each emitter 21, 22 e 23 can be adjusted or oriented independently from one another.

The possibility of adjusting or orienting, in particular, the first emitter 21 and the second emitter 22 allows, as shown in FIG. 4, to accomplish inspection of the products by using the optimal angle for each source, for example without the beams emitted by said emitters intercepting the cap or lid of the products when the products have a low height/diameter ratio, thus solving one of the aforementioned problems of prior art.

In the case of products that are very high with respect to their diameter, the position of the cap does not constitute a limitation for the choice of the angle between the first two emitters, which angle can in this case be near 90 degrees, so as to maximize the probability of detection when the foreign body has a high form factor.

With such products it is preferable that the inspection angle is close to +45 degrees for the second emitter and −45 degrees for the first source, this being the best compromise between the different viewpoints, i.e. 90 degrees, and the product section passed through by the rays + and −45 degrees.

The specific set of angles recommended in the preferred embodiment for the emitters further allows—in the case when ray-generating tubes are oriented so as to have the center of the X-ray beams orthogonal to the corresponding sensors, with the tubes arranged in the intermediate position, and have a beam width of at least 40°—to cover, for example, products in a height range of 40-200 mm without having to change the rotation angle of the X-ray tubes, but merely by changing their position in height.

The use of ray-generating tubes having a sufficiently large aperture therefore allows, with the employed geometries, to realize a substantially simpler machine without altering the performances.

According to other embodiments, the emitters can be fixed and non-orientable or only one or some of them can be orientable, without departing from the scope of what is described and claimed.

In the preferred embodiment, the three linear sensors, the first one 31, the second one 32 and the third one 33, preferably having a flat structure, are arranged as follows:
  the first sensor 31 and the second sensor 32, oriented so as to be orthogonal to their respective emitters, when the orientation angle of said emitters, if they are orientable relative to the horizontal plane, is an intermediate angle among the predetermined values;
  the third sensor 33, instead, is arranged in a substantially vertical position.

Each sensor is in any case orthogonal to the vertical plane including the corresponding source.

According to further embodiments, the sensors can have a non-flat shape, without departing from the scope of what is described and claimed.

The Applicant has verified, through experiments, that the possibility of varying the height and/or angle of the emitters, in the preferred case in which the emitters are orientable, does not such as to modify the quality of inspection in its whole.

In addition, the Applicant has noticed that the use of X-ray emitters with small focus and, preferably, compact size, for example made by tubes fed by different generators, allows to realize an assembly of emitters/sensors adapted to give ample freedom of movement and rotation of the X-ray beams, with the consequent advantage that products with even very different sizes can be inspected, as for each product it is possible to use an optimal set of angles.

Obviously, in the case of products with constant size, the need of having ample freedom of movement and rotation of the X-ray beams may not be required and therefore it is possible to provide for the use of sets of emitters/sensors having a fixed position, without departing from the scope of what is described and claimed.

The use of a X-ray emitter with small focus, for example lower than 1 millimeter, justifies the use of a geometry in which the product is located in a position distant from the sensor, allowing to take advantage of the effect of perspective generated by the projection without this entailing significant blurring of the edges of the captured image of the product.

Figure 5:
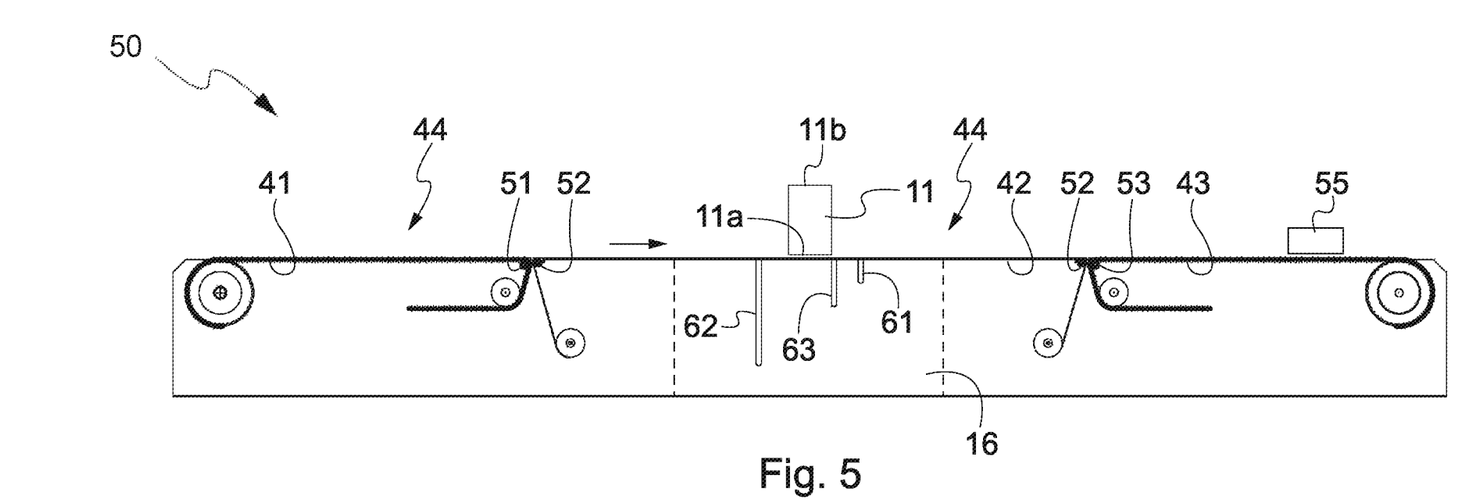
FIG. 5 and FIG. 6 schematically show side and top views, respectively, of a kind of conveying apparatus provided in the machine.
Figure 6:
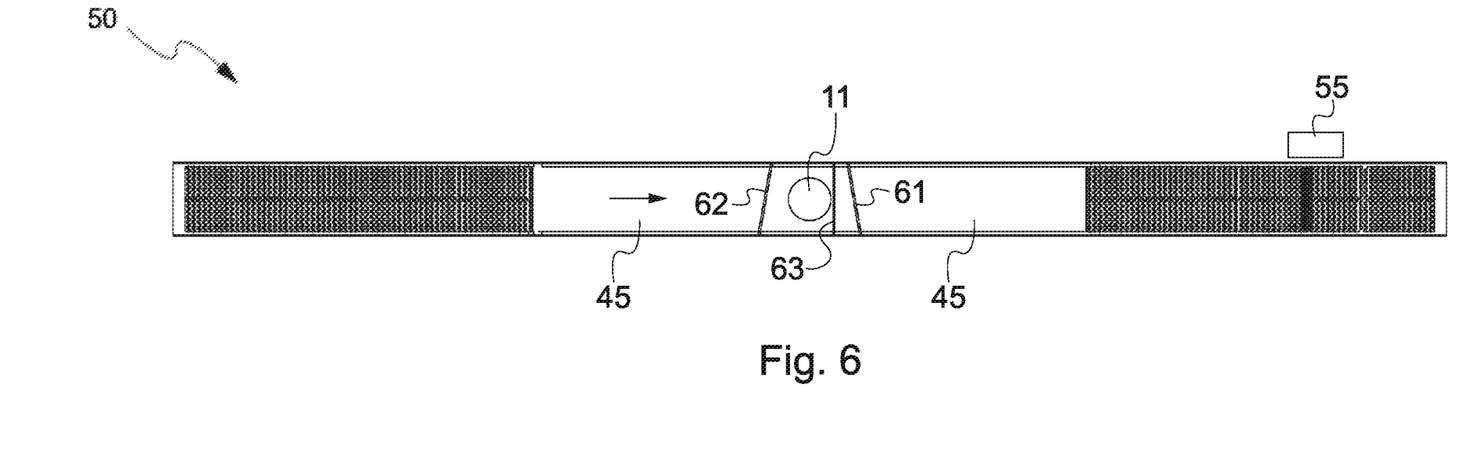
Figure 7:
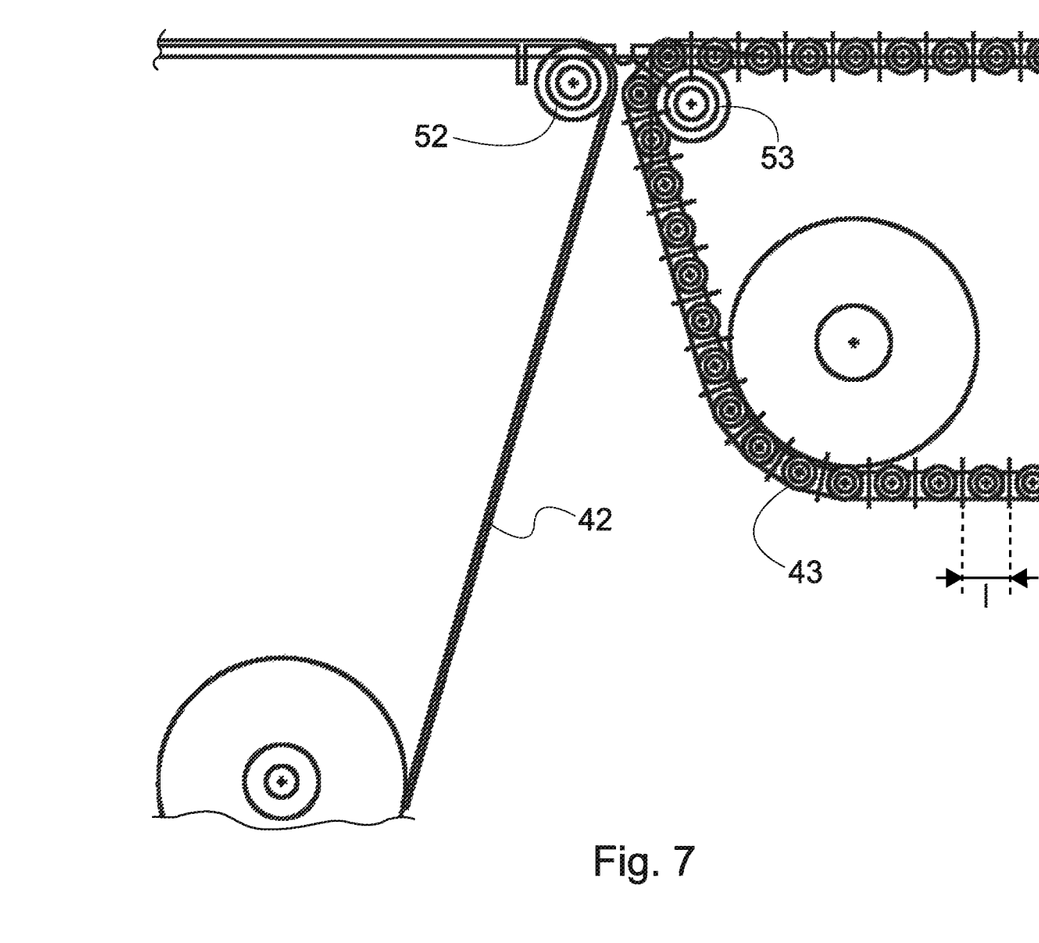
FIG. 7 shows a detail of the conveying apparatus of FIG. 5.

Referring to FIG. 5-7, there is described the conveying apparatus 40 which comprises, in the preferred embodiment, at least a first conveyor belt or input belt 41, a second conveyor belt or inspection belt 42 and at least a third conveyor belt or exit belt 43 arranged end-to-end in cascade for transporting the products 11, and having respective portions along the tunnel 15 corresponding to an input section, an inspection section and a section for possible discarding.

According to the preferred embodiment, it is provided that the machine 10 is inserted in a production line and that the inlet passage and the outlet passage respectively into and out of the production line take place in a known manner, for example by lateral translation assisted by shaped fixed side guides.

Preferably, the first conveyor belt 41 and the third conveyor belt 43 are modular belts, preferably with high resistance to wear, non-transparent to X-rays, for example belts Model UNI_M-QNB_C_K600 from the Company AMMERAAL BELTECH.

These two belts run over a metal surface 45, for example made of steel, either in direct contact therewith or, preferably, on low friction support, of known type, lying on the metal surface.

In the example of the preferred embodiment, the input belt 41 and the exit belt 43 are of the modular type with standard size mesh, for instance a mesh size with a pitch of ½ inch (12.7 mm).

The Applicant has found that this pitch is small enough to guarantee regular passage of the products between the first belt 41 and the second belt 42, while being still a standard size, highly durable and easily purchasable from several manufacturers of modular chains made of different materials and with different surface configurations.

According to other embodiment, the mesh of the first belt and of the third belt, depending on the size of the products, can range, for instance, from ¼" to 1.0" (from 6.35 mm to 25.4 mm) with a modular type, standard size mesh.

In the preferred embodiment, the second belt 42 is a carpet belt substantially transparent to X-rays, for example a carpet belt made of canvas, rubber canvas or rubber.

This belt is preferably positioned so as to cross the inspection zone 16 and, for example, is a belt Model ROPANYL EM 4/1 0+02 light blue M2 FG from the Company AMMERAAL BELTECH.

Preferably, this belt runs directly over the metal surface 45.

According to the preferred embodiment, it is provided that the passage between the input belt 41 and the inspection belt 42 and the passage between the inspection belt 42 and the exit belt 43 take place by end-to-end abutment of end rolls 51, 52, 53 of the belts and thereof of the belts themselves. This passage is made possible by the choice of the belt types, of the winding diameters of the end rolls and of the relative speeds of the belts.

Merely by way of example, in the case when the maximum transport speed of the products in the tunnel 15 of the machine is about 60 m/minute, it is provided that the end rolls 51 and 53 of the first belt 41 and of the second belt 43, respectively, are about 25.4 mm and that the diameter of the end rolls 52 of the second belt 42 is preferably smaller than that of the first and third belts, owing to the characteristics of said second belt.

Obviously, in order to prevent possible tilting of the products, the transport speed of all the belts must be essentially identical, if it is provided to keep the distance among the products constant, or be comprised in a range of +/−10%, if it is provided to vary the distance among the products.

For example, when it is provided to increase the distance among the products in the inspection section and in the section for possible discarding, the speed of the second belt and of the third belt can be higher than the speed of the first belt, within the range indicated above.

Preferably, it is provided that the length of the transport section of the first belt 41 along the tunnel 15 is determined experimentally so as to ensure regular passage of the product from the input belt 41 to the inspection belt 42.

Similarly, the length of the transport section of the inspection belt 42 along the tunnel 15 is, preferably, determined experimentally, in order to ensure the dampening of oscillations of the product possibly due to the passage between the input belt and the inspection belt before the inspection zone 16.

The length of the transport section of the exit belt 43 along the tunnel 15 is, preferably, determined so as to ensure the space necessary for transferring the products onto the exit belt, and to allow, for example, the provision of a discarding device 55, of known type, along the exit belt, adapted to allow to remove from the production line those products exhibiting anomalies at the inspection step.

According to the preferred embodiment, the metal surface 45 over which the second belt 42 runs has, in correspondence of the emitters 21, 22 and 23, respective slots 61, 62 and 63 (FIG. 5 and FIG. 6).

The slots allow the passage of X-rays emitted by the emitters 21, 22 and 23 so that they reach the respective sensors 31, 32 and 33 without being obscured by the metal surface 45. The metal surface provides an extremely robust and simple structure that is not weakened by the slots, whereby the whole consisting of the metal surface and the slots is such as to allow the transport of products of very variable sizes, though in a context in which there are provided emitters positioned above and below the horizontal supporting plane.

Merely by way of example it is reported here that an inspection machine 10 having the architecture described above allows inspection of products arranged on the conveyor belts at a minimum distance comprised at least between 1 mm and 10 mm and with a cross section comprised at least between 10 and 100 mm and a height along the vertical axis comprised at least between 40 and 200 mm.

Of course, products with other dimensions can be inspected by using the above indications, without departing from the scope of what is described and claimed.

The operation of an inspection machine 10, for example including three emitters 21-23, three sensors 31-33 and a conveying apparatus 40 is as follows.

In a first step or calibration step, if provided, it is envisaged, see FIG. 4, that the first emitter 21 and/or the second emitter 22 is/are oriented so as to obtain an optimal projection of the bottom of the product to be examined, while at the same time avoiding that the projection of any cap or lid of the product, in particular when made of metal, overlaps the image of the bottom. It is also envisaged that the third emitter 23 is oriented so as to illuminate the upper zone of the product, being located at a level corresponding to the zone facing the upper zone or the cap.

In a second step, the machine 10, preferably already inserted in the production line, is fed with the products to be inspected at the same speed of the production line so that the products travel through the inspection zone 16 and emitters 21, 22 and 23 cooperate with the respective sensors 31, 32 and 33 to carry out layer-by-layer the inspection of each product.

Figure 3:
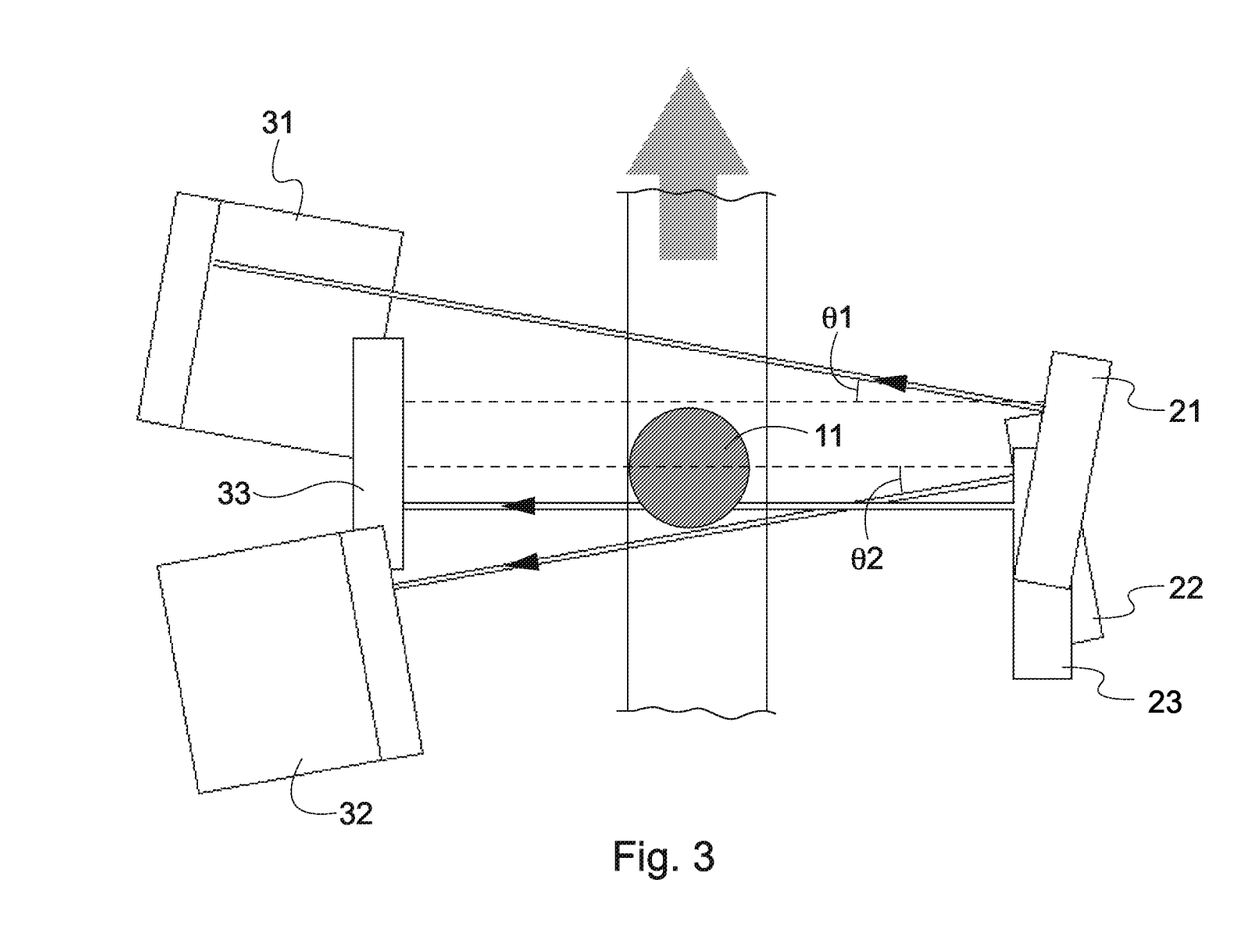
FIG. 3 is a schematic top illustration of the pairs of X-ray emitters/sensors in a top view of the machine of FIG. 1.

In the illustrated embodiment, it is also envisaged that each product is inspected by each source/sensor pair at different times in the inspection zone as shown in FIG. 3.

In particular, in the preferred embodiment, it is provided that the emitters are inclined on a plane corresponding to the transport plane with respect to the perpendicular to the transport direction at angles θ1 and θ2, respectively, for example between ±10 degrees, so as to obtain two substantially different images of the relative positions between the projection of the container wall and that of any foreign body to be detected and situated, for example, in proximity of such wall.

Of course, nothing prevents that, according to variants of the described embodiment, two or more source/sensor pairs work simultaneously in the inspection zone 16 on the same product or that the emitters are inclined on a plane corresponding to the transport plane along the transport direction at angles other than those indicated, for example ±20 degrees, the angle between the emitters 21 and 22 differing of at least 20 degrees within the described range.

Once the inspection is completed, it is envisaged that in a third step the defective products are ejected from the exit belt 43 by means of the discarding device 55 before the products that are considered acceptable are inserted in the production line so that the production line only contains those products that are considered acceptable.

The operation described above, intended for the machine 10 in its maximum configuration, can easily be simplified in the case there is no provision, for example, of the third source/sensor pair 23, 33 or in the case in which the discarding device is not provided along the exit belt 43 or in the case in which one or more emitters are not orientable depending on the dimensional characteristics of the products.

The machine 10, as described, by providing, preferably, multiple emitters with orientation such as to cover not only the bottom of the products but also the upper area, including the cap, allows to maximize the benefits of a multi-view system.

In fact, the product zones with lower contrast in the image relating to a view from above or view from below obtained with a source/sensor pair, corresponding to the passing through a greater thickness of the product, appear instead in greater contrast in images obtained with another source/sensor pair, as they correspond to the passing through a smaller thickness of the product.

Moreover, the choice of using, preferably, great angles between the two views, from above and below, for example comprised between 36 and 90 degrees, allows to analyze foreign bodies from two very different viewpoints, increasing significantly the likelihood of detecting foreign bodies in the product, in the case in which the foreign body has very irregular shape.

In the preferred embodiment, in the case in which the X-ray emitters are not fixed in a predetermined position, these may be arranged from time to time at an angle that is the best compromise between coverage of the volume of the product, projection of the bottom zone and product thickness through which the rays pass, thus maximizing the advantages described above.

The Applicant, in particular, has also found that, in the case of X-ray orientable emitters, arranged above and below the horizontal plane, the angles between the emitters are not independent of the geometric characteristics of the products and may not be symmetrical with respect to the horizontal plane, in particular in the case where there is a strong need to avoid that the rays emitted by the X-ray emitter arranged above the horizontal plane are subject to any interference due, for example, to a metal cap.

The proposed layout is innovative in defining the optimal angles for inspection of the maximum volume of product, with a greater attention to the bottom, but without forgetting the need to detect foreign bodies and non-uniformities in the entire volume of the product as well as the importance, for some types of products, of having a reliable control of the zone near the cap.

Moreover, preferably, an inclination of 20 degrees in total, for example ±10 degrees, between the two beams, obtained with the angles θ1 and θ2 of inclination of the emitters 21 and 22 with respect to the perpendicular to the transport direction, used in the preferred embodiment, allows to have in any case, in at least one of the two images, the projection of the foreign body possibly present in contact with the container side wall distant from the low sensitivity zone formed by the projection of the wall itself in the image.

The relatively low value chosen for the θ1 and θ2 inclination of the x-generating emitters, provided for in the preferred embodiment, further allows to maintain an extremely small space, for example less than 5 mm, between successive products, thus allowing to insert the machine in production lines without the need to use spacer devices between one product and the other in the production lines or in the machine.

Obviously, in other embodiments, the spacing between the products can also be greater than the indicated one, if the inclination the θ1 and θ2 between the beams is, for example, greater than ±10 degrees.

The machine 10 as proposed in its configuration with three emitters/sensors is such as to ensure a complete coverage of the product, with a greater number of views concentrated in those zones where the probability of finding foreign objects is greater, i.e. bottom and cap zones.

In the case of a machine with two emitters/sensors, this configuration allows to ensure complete coverage of the bottom, by inspecting each zone with the most favorable angle therefor, if the emitters are orientable, or, if they are not orientable, where products are of constant size over time.

The machine 10, by providing in any case sensors oriented in a fixed position in space, ensures the most uniform irradiation that can be obtained.

Furthermore, as the sensors, preferably, have a flat geometry, this allows, for example, the use of standard linear sensors of different brands and models of linear sensors, while at the same time maintaining limited dimensions and ease in maintenance operations, when required.

The machine 10, by providing a conveying apparatus 40 having, preferably, three belts is an improvement over the prior art, which provides for the use of only one belt directly adjoining the production line, because:

it allows to obtain a standard combination of production line and machine belt;

it manages, within the machine, the passage from/to the input and exit belts on one hand and the inspection belt on the other hand, which, according to the described exemplary embodiment, have, preferably, different friction with the products, the inspection belt being a belt transparent to X-rays.

In summary, the passage from/to belts with different frictions does not occur from/to the production line and the inspection belt, but from/to belts within the inspection machine, and therefore under more controllable conditions.

The end-to-end passage from/to input belt, inspection belt and exit belt reduces any problems related to the different coefficients of friction of the belts and tend to avoid wear or breakage of the inspection belt, which, being transparent to X-rays, usually has mechanical properties of strength and friction different from those of the input and exit belts.

Moreover, the end-to-end transfer of the products allows use of uniform speeds of the belts without the possibility of the occurrence of the sped components orthogonal to the transport direction of the products, which could lead to premature wear of the inspection belt.

In addition, the proposed method of end-to-end transfer allows to bring the products from the chain non-transparent to X-rays to the inspection belt transparent to X-rays without the need to use complex mechanical devices adapted to accompany the passage, for example screw conveyors, straps, star-shaped holders, known per se, which, in addition to being more difficult to manage, could damage the label that may be present on the products.

Of course, obvious changes and/or variations are possible to the above description, in dimensions, shapes, materials, components and connections as well as in the details of the illustrated construction and of the method to operate without departing from the invention as specified in the following claims.

The invention claimed is:

1. A non-destructive X-ray inspection machine for individually packaged products having a bottom and a lid or cap in separate zones, said machine comprising:
   a conveying apparatus having a transport plane and a transport direction and adapted to convey said products along a transport direction with the bottom resting on the transport plane;
   at least two X-ray emitters adapted to emit X-rays so that said X-rays pass through said products at a top-to-down angle and at a down-to-top angle, respectively, relative to the transport plane, in an inspection zone comprised in said transport plane; and
   at least two X-ray sensors, one for each of said at least two X-ray emitters, said X-ray sensors being oriented so as to be orthogonal to a vertical plane including the corresponding X-ray emitter;
   wherein at least one of said two emitters is freely orientable in angle, within a predetermined range, relative to the transport plane, whereby the bottom of the product is inspectable without the X-rays of said two emitters intercepting said lid or cap of said products;
   wherein at least one of said two X-ray emitters is inclined on a plane corresponding to the transport plane at an angle comprised between −20 and +20 degrees relative to perpendicular to the transport direction lying on the transport plane, and wherein said angle relative to perpendicular to the transport direction of at least one of said two emitters is at least 20 degrees relative to the angle relative to perpendicular to the transport direction of the other one of said two emitters.

2. The machine according to claim 1, wherein said at least one of said two emitters is freely adjustable in height, within a predetermined range, relative to the transport plane.

3. The machine according to claim 1, wherein both said emitters are freely adjustable in height within a predetermined range relative to the transport plane.

4. The machine according to claim 1, wherein both said emitters are freely orientable in angle within a predetermined range relative to the transport plane.

5. The machine according to claim 1, wherein an angle of about 90 degrees measured with reference to the transport plane is provided between the two emitters.

6. The machine according to claim 1, further comprising:
   a third X-ray emitter adapted to emit X-rays so that said X-rays pass through said products in a direction orthogonal to the transport direction, in the inspection zone for said products.

7. The machine according to claim 6, wherein it is provided that said third X-ray emitter is freely orientable in angle, within a predetermined range, relative to the transport plane, so as to align said third X-ray emitter, in use, near said lid or cap of said product and to inspect both the zone where said lid or cap is provided and an upper zone of the product.

8. The machine according to claim 7, wherein it is provided that said third X-ray emitter is adjustable in height, within a predetermined range, relative to the transport plane.

9. The machine according to claim 6, wherein it is provided that said third X-ray emitter is adjustable in height, within a predetermined range, relative to the transport plane.

10. The machine according to claim 1, wherein a first one of said two emitters is orientable over an angle ($\beta$) comprised between −18 and −55 degrees relative to the transport plane; and wherein a second one of said two emitters is orientable over an angle ($\alpha$) comprised between +18 and +55 relative degrees to the transport plane.

11. A method for operating an X-ray inspection machine for individually packaged products having a bottom and a lid or cap in separate zones, said machine comprising a conveying apparatus having a transport plane adapted to convey said products with the bottom resting on the transport plane, at least two X-ray emitters located above and below said transport plane and at least two X-ray sensors, one for each of said at least two X-ray emitters, the method comprising the steps of:
   freely orienting in angle at least one of said two emitters, within a predetermined range, relative to the transport plane of said machine;
   inclining at least one of said two X-ray emitters on a plane corresponding to the transport plane at an angle comprised between −20 and +20 degrees relative to perpendicular to the transport direction lying on the transport plane, said angle relative to perpendicular to the transport direction of at least one of said two emitters being at least 20 degrees relative to the angle relative to perpendicular to the transport direction of the other one of said two emitters; and
   obtaining an image of the bottom of the product, neither hidden nor distorted by the projection of the lid or cap.

12. The method according to claim 11, wherein, when said machine comprises at least a third X-ray emitter, said method comprises the further steps of:
   freely orienting in angle said third X-ray emitter, within a predetermined range, relative to the transport plane so as to align said third X-ray emitter to said lid or cap of said products; and
   inspecting both the zone where said lid or cap is provided and an upper zone of the product, as a function of dimensional characteristics of said products.

13. The method according to claim 12, wherein said method comprises the further step of freely adjusting in height said third X-ray emitter, within a predetermined range, relative to the transport plane of said machine.

14. The method according to claim 11, further comprising the step of freely adjusting in height said at least one of said two emitters, within a predetermined range, relative to the transport plane of said machine.

15. The method according to claim 11, further comprising the step of freely orienting in angle both said two emitters, within a predetermined range, relative to the transport plane of said machine.

16. The method according to claim 11, further comprising the step of freely adjusting in height both said two emitters, within a predetermined range, relative to the transport plane of said machine.

* * * * *